(12) United States Patent
Al Mansour

(10) Patent No.: US 10,667,840 B2
(45) Date of Patent: Jun. 2, 2020

(54) MECHANICAL GUN-TYPE CIRCUMCISION DEVICE WITH GLANS PROTECTION SYSTEM FOR SAFE CUTTING AND CAUTERIZATION OF THE FORESKIN

(71) Applicant: UNIVERSITA' DEGLI STUDI DI ROMA 'LA SAPIENZA', Rome (IT)

(72) Inventor: Monir Al Mansour, Rome (IT)

(73) Assignee: UNIVERSITA' DEGLI STUDI DI ROMA 'LA SAPIENZA' (IT)

( * ) Notice: Subject to any disclaimer, the term of this patent is extended or adjusted under 35 U.S.C. 154(b) by 286 days.

(21) Appl. No.: 15/572,003

(22) PCT Filed: May 6, 2016

(86) PCT No.: PCT/IB2016/052597
§ 371 (c)(1),
(2) Date: Nov. 6, 2017

(87) PCT Pub. No.: WO2016/181271
PCT Pub. Date: Nov. 17, 2016

(65) Prior Publication Data
US 2018/0344342 A1    Dec. 6, 2018

(30) Foreign Application Priority Data
May 8, 2015    (IT) .................. 102015000014334

(51) Int. Cl.
*A61B 17/326*    (2006.01)
*A61B 90/00*    (2016.01)
(Continued)

(52) U.S. Cl.
CPC .... *A61B 17/326* (2013.01); *A61B 2017/0042* (2013.01); *A61B 2017/320052* (2013.01); *A61B 2090/035* (2016.02); *A61B 2090/036* (2016.02)

(58) Field of Classification Search
CPC ................................... A61B 17/326
See application file for complete search history.

(56) References Cited

U.S. PATENT DOCUMENTS 3,111,124 A    11/1963    Rodbard
2004/0215210 A1    10/2004    Duel
(Continued)

FOREIGN PATENT DOCUMENTS

CN    203598017 U    5/2014
EP    2606839 A1    6/2013

OTHER PUBLICATIONS

International Search Report for PCT/IB2016/052597 dated Aug. 12, 2016.

*Primary Examiner* — Todd J Scherbel
(74) *Attorney, Agent, or Firm* — Thomas | Horstemeyer, LLP

(57) ABSTRACT

Circumcision device including a housing (10) comprising a handgrip part (13) and a control member (15), a guide part (20) comprising a stem (21) and a shearing template (23) fixedly arranged on a distal end of the stem (21), said shearing template having a concave distal surface (23*a*) and a side surface (23*b*) tapered in the proximal direction, a pair of arms (30, 30'), each having a distal end provided with a semi-annular blade (31, 31'), each arm being rotatable about an axis (y, y') perpendicular to the extension direction of the stem (21), between an open position and a shearing position in which the semi-annular blades (31, 31') are closed to form a ring perpendicular to the extension axis of the stem (21) and have a cutting edge (32, 32') which engages the side surface (23*b*) of the shearing template (23), and an actuating mechanism (40) for controlling rotation of the arms (30, 30') in response to an actuation of the control member (15).

14 Claims, 5 Drawing Sheets

(51) Int. Cl.
 A61B 17/00 (2006.01)
 A61B 17/32 (2006.01)

(56) References Cited

U.S. PATENT DOCUMENTS

2010/0168757 A1* 7/2010 Tomlinson ........... A61B 17/326
 606/118
2013/0079795 A1 3/2013 Starr

* cited by examiner

MECHANICAL GUN-TYPE CIRCUMCISION DEVICE WITH GLANS PROTECTION SYSTEM FOR SAFE CUTTING AND CAUTERIZATION OF THE FORESKIN

CROSS-REFERENCE TO RELATED APPLICATION

This application is the 35 U.S.C. § 371 national stage application of PCT Application No. PCT/IB2016/052597, filed May 6, 2016, where the PCT claims priority to and the benefit of, IT Patent Application No. 102015000014334, filed May 8, 2015, both of which are herein incorporated by reference in their entireties.

The present invention relates in general to circumcision techniques.

Circumcision is a respected religious ritual which is so well-established that, on occasions, it is performed without minimum guarantees as regards safety or protection of the anatomy of the glans. Consequently, the injury resulting from the use of inappropriate procedures is extensive, both for the patient, who is obliged to resort to plastic and reconstructive surgery, and for the national health service, which must assume the costs thereof.

In some cases circumcision is also required in order to correct certain pathologies of the male genital organ.

The circumcision operations are usually carried out with the aid of clips which tension the foreskin which to be removed using a scalpel. Also known are circumcision devices, such as that described in the document EP U.S. Pat. No. 2,606,839 A1, which consists of a ring which, on the one hand, performs easy cutting of the phimosis, but on the other hand does not respect the anatomy of the glans. In addition no provision is made for cauterization.

One object of the present invention is to provide a circumcision device which is both simple and safe to use.

Another object is to provide a device which may be realized in a particularly low-cost manner so that it may be used in particular as a disposable tool.

In view of these objects, the invention relates to a circumcision device which includes:
 a housing comprising a handgrip part integral with the housing, wherein at least one control member is arranged on the handgrip,
 a guide part comprising a stem integral with the housing, said stem being arranged partially within the housing and outwardly protruding through an opening of the housing, and a shearing template fixedly arranged on a distal end of the stem, said shearing template having a concave distal surface and a side surface tapered in the proximal direction,
 a pair of arms, each having a distal end provided with a semi-annular blade, each arm being rotatable about an axis perpendicular to the extension direction of the stem, between an open position and a shearing position in which the semi-annular blades are closed to form a ring perpendicular to the extension axis of the stem and have a cutting edge which engages the side surface of the shearing template, and
 an actuating mechanism for controlling rotation of the arms in response to an actuation of the control member.

The gun-type anatomical device forming the subject of the present invention guides the surgeon so as to perform a perfectly round cut perpendicular to the axis of the penis, since the tip of the glans is inserted inside the distal concavity of the shearing template and the axis of the shearing template and that of the penis coincide. The blades, with closing of the gun, perform a cut perpendicular to the axis of the stem, plus a cut in the two side zones where the two blades touch each other.

The present apparatus may be designed as a disposable device protected by a container with a sterile atmosphere inside. This device, if used observing the appropriate hygienic requirements and respecting the anatomy of the glans, ensures a correct and optimum procedure.

Preferred embodiments of the invention are defined in the dependent claims which are to be understood as forming an integral part of the present description.

Further characteristic features and advantages of the device according to the invention will become clear from the following detailed description of an embodiment of the invention, provided with reference to the accompanying drawings which are provided purely by way of a non-limiting example and in which:

FIGS. 2a and 2b are, respectively, a cut-away view and a simplified view of the device according to FIG. 1 and a view, on a larger scale, of a detail of FIG. 2a;

Figure 1:
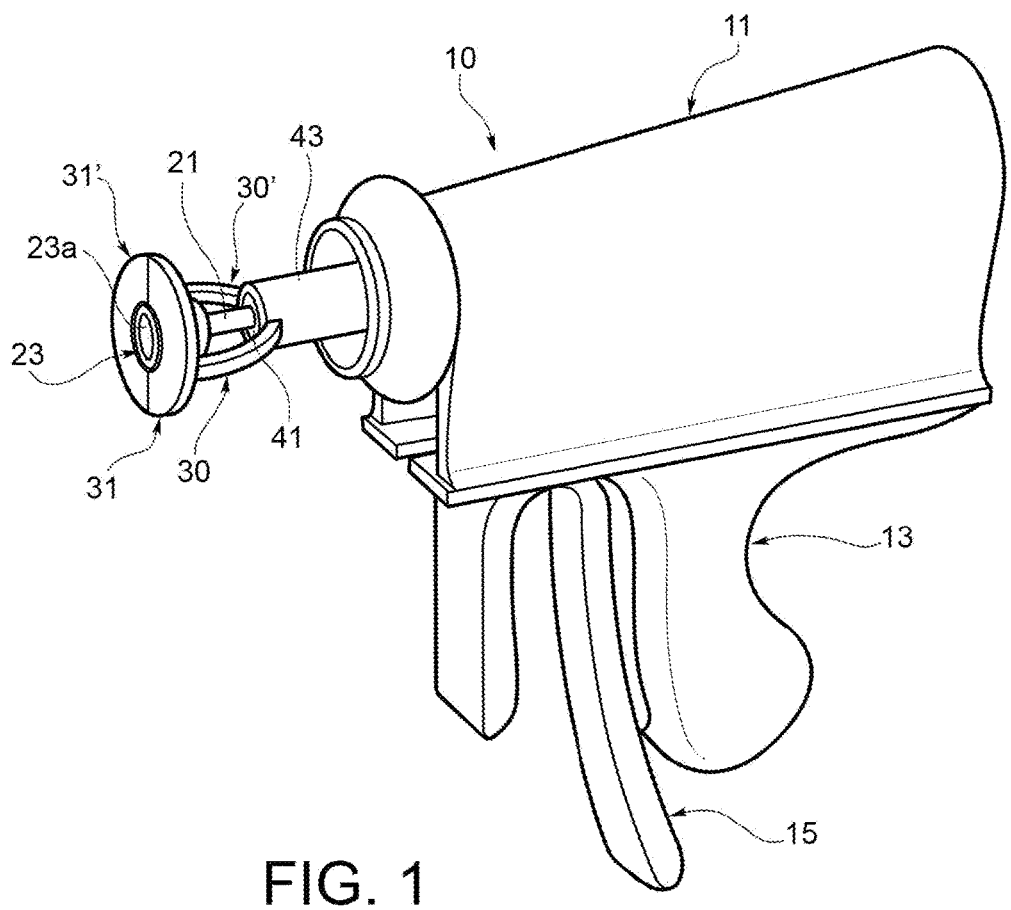
FIG. 1 is a simplified perspective view of a circumcision device according to the present invention.
Figure 2B:
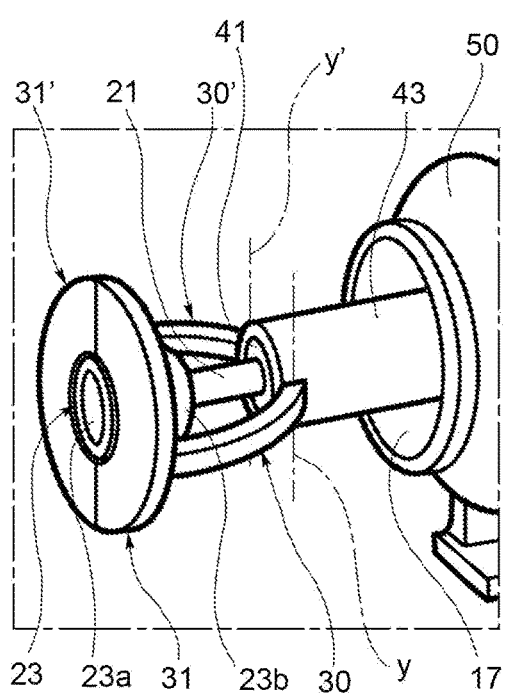
Figure 2A:
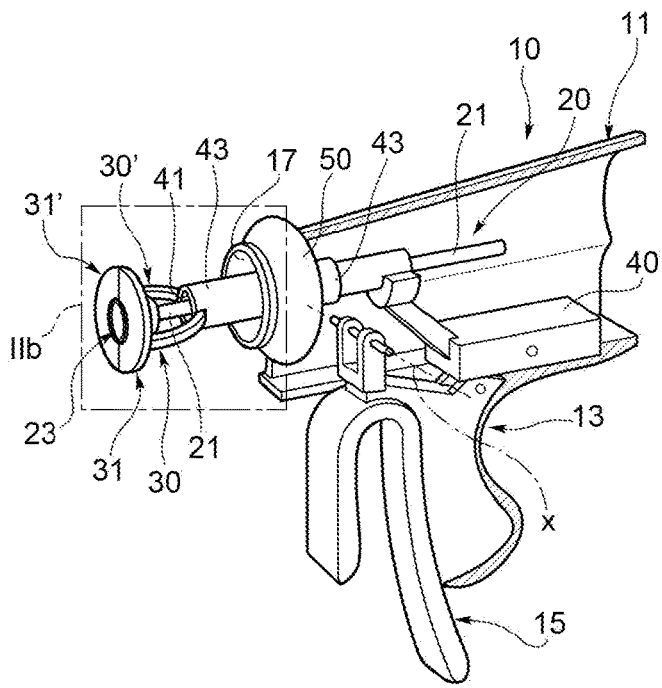

With reference to FIGS. 1, 2b-2a, 3a-3e, these figures show a circumcision device including a housing 10 which is made of plastic and which comprises a main housing part 11 and a handgrip part 13 integral with the housing 10. At lest one control member 15 is arranged on the handgrip part 13. In the example shown the control member 15 consists of a lever which can be actuated manually and which is hingeably mounted on the housing 10 and is rotatable about a transverse axis x (FIG. 2a).

With reference to FIG. 2a, the device also includes a guide part 20 comprising a stem 21 integral with the housing 10 and a shearing template 23 arranged fixed on a distal end of the stem. The stem 21 is arranged partially inside the housing 10 and protrudes outwardly though an opening 17 of the housing 10. The shearing template 23 has a substantially bell-like form and has a concave distal surface 23a and a side surface 23b tapered in the proximal direction.

Figure 7:
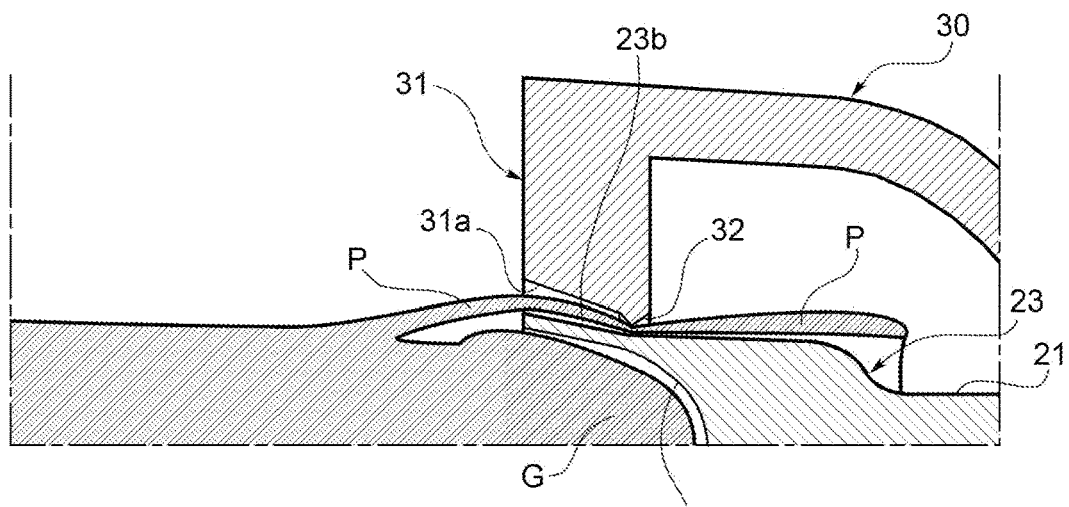
FIGS. 4 to 8 are simplified perspective views illustrating the method for using the device according to FIG. 1.
Figure 3A:
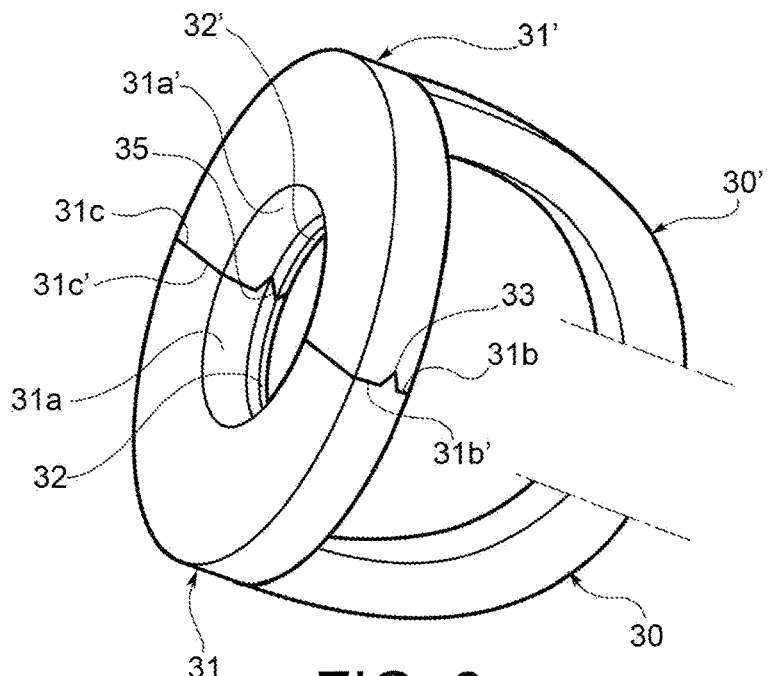
FIGS. 3a-3e are, respectively, a view of a pair of arms provided with blades of the device according to FIG. 1, a detail on a larger scale of FIG. 3b, a view of each of the arms provided with a blade, and a view of a blade with respective cutting edges.
Figure 3B:
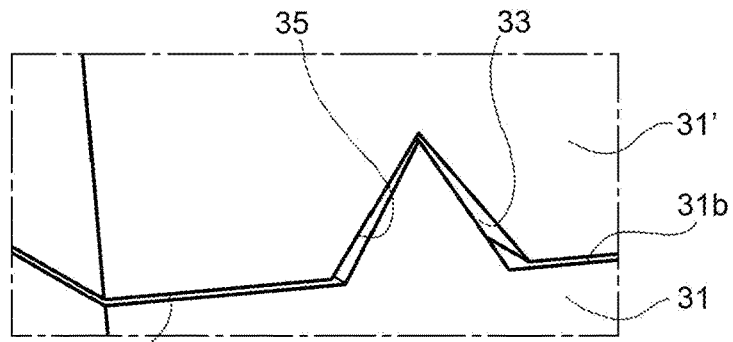
Figure 3C:
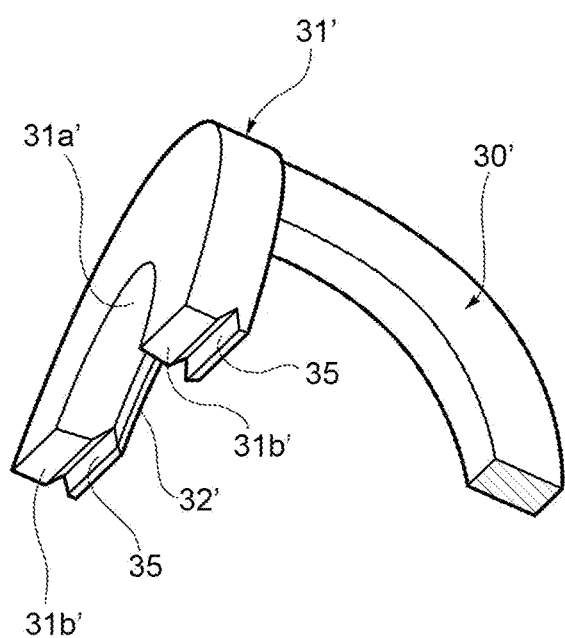
Figure 3D:
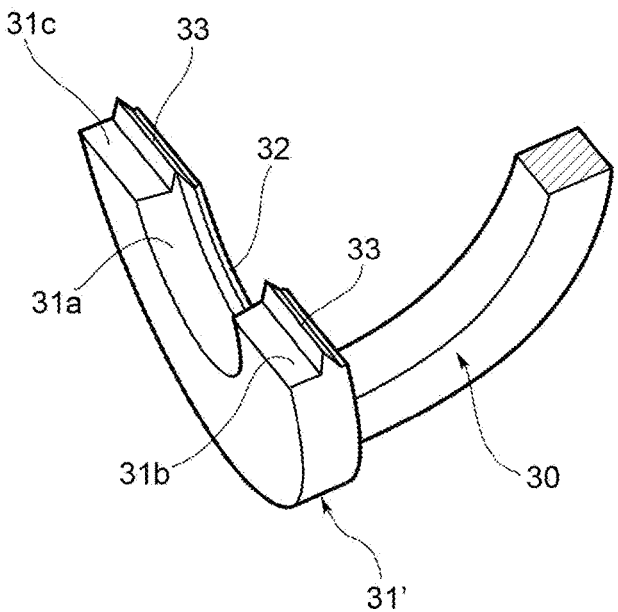
Figure 3E:
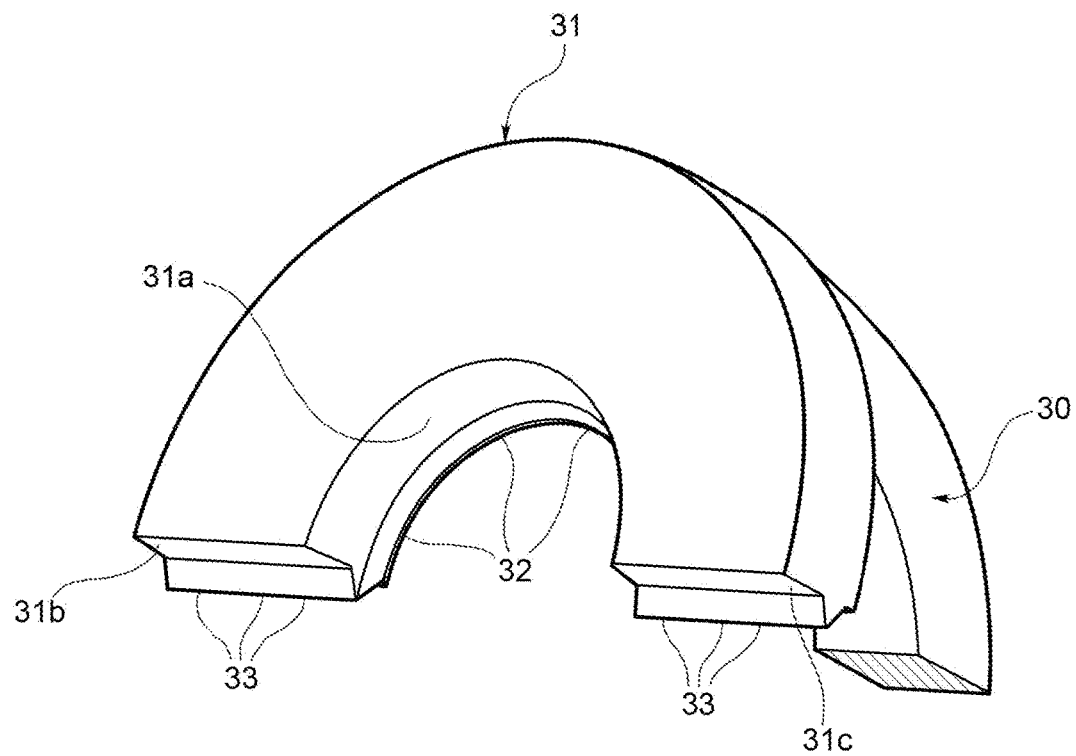
Figure 5:
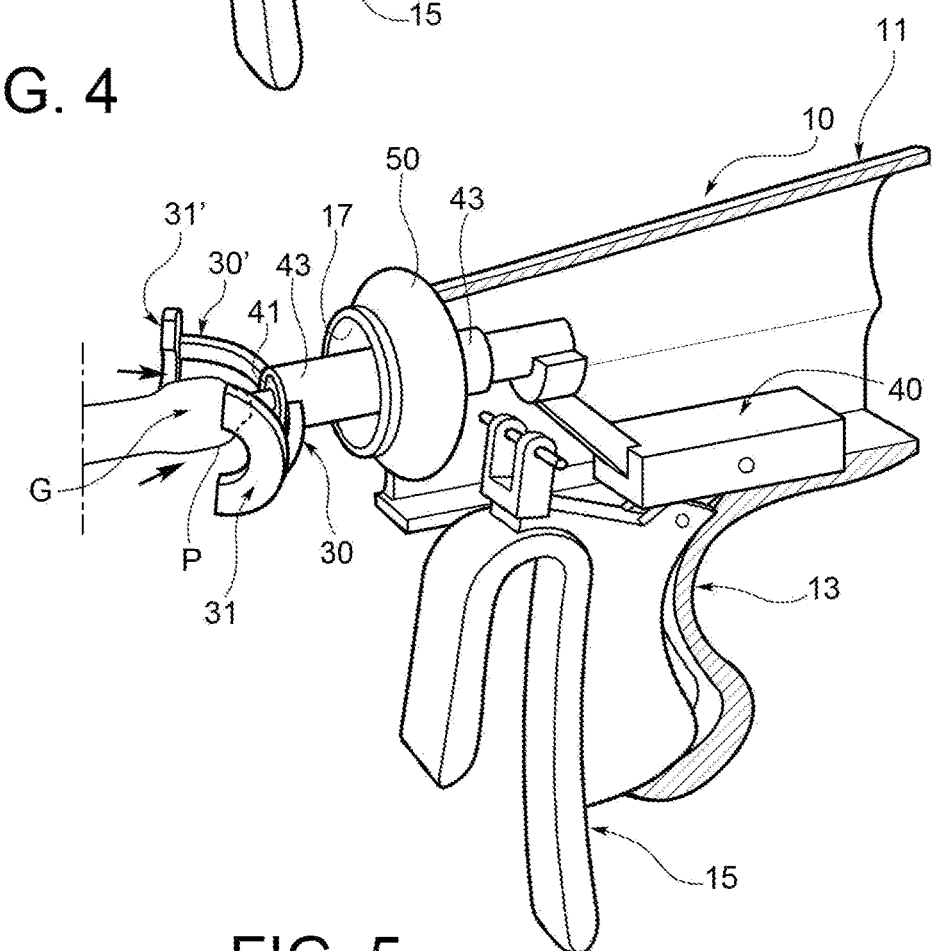
Figure 8:
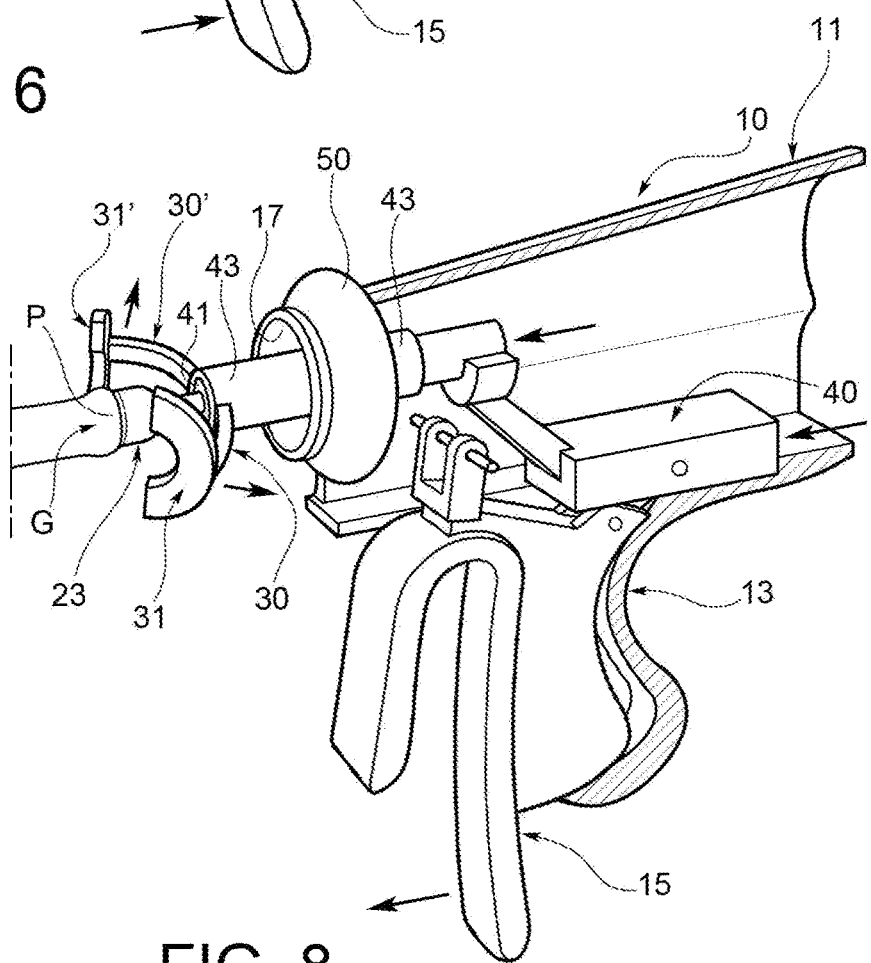

The device also includes a pair of arms 30, 30' each having a distal end which is provided with a semi-annular blade 31, 31' made of medical grade metal. Each arm 30, 30' is rotatable about an axis y, y' perpendicular to the direction of extension of the stem 21, between an open position (shown in FIGS. 5 and 8) and a shearing position in which the semi-annular blades 31, 31' are closed to form a ring perpendicular to the extension axis of the stem 21. In the shearing position the semi-annular blades 31, 31' have a cutting edge which engage the side surface 23b of the shearing template 23 (see FIG. 7).

With particular reference to FIGS. 3a-3e, each semi-annular blade 31, 31' has a main working surface 31a, 31a' having a curved profile tapered in the proximal direction and a pair of secondary working surfaces 31b, 31c; 31b', 31c' arranged on diametrically opposite sides of the main working surface 31a, 31a' of the respective blade 31, 31'. A curved cutting edge 32, 32' is provided on the main working surface 31a, 31a', which cutting edge forms a circular closed curve when the blades are in the shearing position. Furthermore, when the blades in the shearing position, the secondary working surfaces 31b, 31c of one of the blades engages the working surfaces 31b', 31c' of the other blade. The pair of secondary working surfaces 31b, 31c of one of the blades is provided with a secondary cutting edge 33; the other pair of secondary working surfaces 31b', 31c' is provided with a groove 35 designed to receive the respective secondary cutting edge 33 when the blades are in the shearing position (see in particular FIG. 3b).

The device also includes an actuating mechanism 40 for performing rotation of the arms 30, 30' in response to an actuation of the control member 15. In particular, the actuating mechanism comprises an inner barrel 41 and an outer barrel 43 arranged coaxially with the stem 21. The inner barrel 41 is arranged translationally integral with the stem 21, while the outer barrel 43 is arranged translatable along it. The actuating mechanism also comprises further components which connect the lever 15 to the outer barrel 43 and have the function of converting the rotary movement of the lever 15 into the translational movement of the outer barrel 43. This mechanism may comprise for example an articulated quadrilateral.

Each arm 31, 31' has a proximal end hinged together with the inner barrel 41 (along the respective axis y, y') and can be rotationally actuated by a translation of the outer barrel 43. For this purpose an articulation (not shown), which connects the respective arm 31, 31' to the outer barrel 43, may be provided. The actuating mechanism 40 therefore causes translation of the outer barrel 43 in response to an actuation of the control member 15 and then, by means of the translation of the outer barrel 43, causes rotation of the arms 30, 30'.

The actuating mechanism 40 may comprise a spring (not shown) or other resilient elements for biasing the arms 30, 30' into the open position. Consequently, actuation of the lever 40 which causes closing of the blades 31, 31' occurs against the resilient force of the spring.

The actuating mechanism 40 may comprise a locking member, for example a ratchet (not shown), which has the function of locking automatically the blades 31, 31' in the shearing position at the end of the closing movement of the arms 30, 30'. In this case a release member, for example a pushbutton (not shown), must be provided, said release member being arranged on the handgrip 13 and being actuatable manually so as to release the blades 31, 31' from the shearing position.

A handling ring 50 rotatable around the stem 21 is arranged on the opening 17 of the housing 10. The handling ring 50 is rotationally integral with the inner barrel 41 and the outer barrel 43. This arrangement allows the entire device to be rotated about an axis of rotation defined by the handling ring 50 and the barrels 41, 43, therefore keeping stationary the arms 30, 30' with the blades 31, 31'. For this purpose, therefore, the part of the actuating mechanism 40 which connects the control member 15 to the outer barrel 43 must be configured so as to allow the rotation of the outer barrel 43 about its longitudinal axis.

Figure 4:
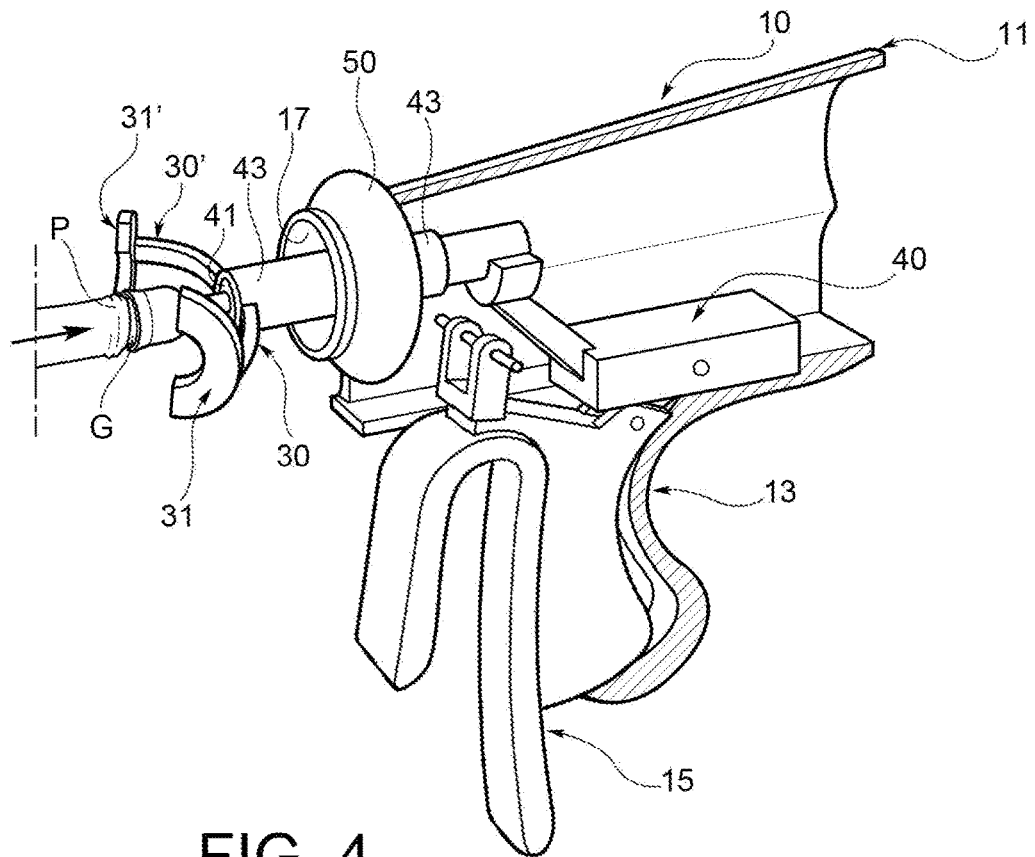
Figure 6:
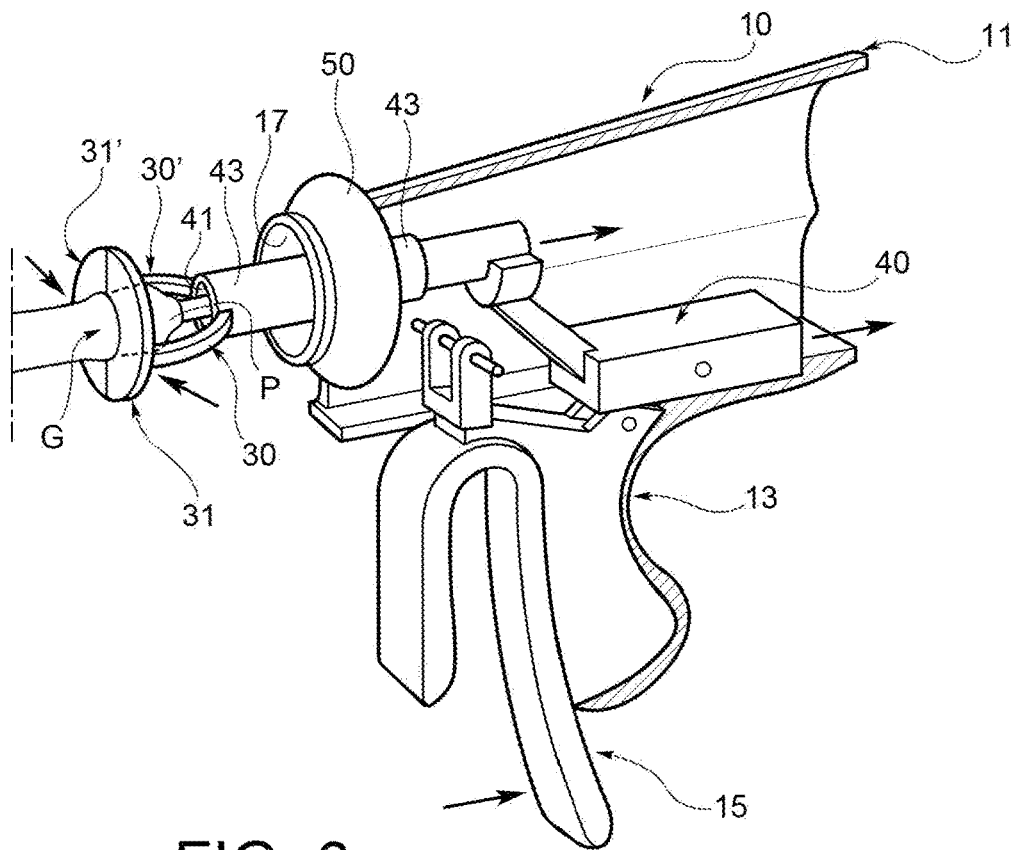

The operation starts with a local anaesthetic, performed by means of injection or ointment, or with sedation. Operationally speaking, the surgeon inserts the concave distal surface 23a of the shearing template 23 over the tip of the glans G (FIG. 4) in order to protect it and slides the foreskin P (FIG. 5) over the outer surface 23b thereof, so that the two membranes of the foreskin are facing the two semi-annular blades. Operation of the lever 15 causes these blades to close (FIG. 6), performing a cut and compressing the end part of the side surface 23b of the bell-type shearing template (where the geometry of the side surface 23b is tapered and has an abrupt variation in inclination—see the circled area indicated by A in FIG. 7). Once cutting has been performed, the device remains locked, the surgeon not being required to exert any force on the lever 15. After a time interval of about two minutes, the surgeon releases the pushbutton, the two blades open again (FIG. 8) and the excess foreskin part is removed. In this way the foreskin is reshaped.

As can be understood, the semi-annular blades once closed coincide in a geometrically perfect manner with the outer surface of the shearing template and perform within a section thereof a circular shaped cut with a zone close to the cut which is compressed and consolidated. It is thus possible to perform a safe mini-invasive operation which may be implemented in a quick and easy manner. The procedure lasts no longer than ten minutes. Once the operation has been terminated, differently from the situation with other apparatus, the patient must merely wear a small, circular, fatty gauze dressing for about two days.

In addition to being used for circumcision, the present device, suitably modified, may also be used to perform circular cuts with dimensions determined by the central shearing template.

The invention claimed is:

1. A circumcision device, comprising:
   a housing comprising a handgrip part integral with the housing, wherein at least one control member is arranged on the handgrip part,
   a guide part comprising a stem integral with the housing, said stem being arranged partially within the housing and outwardly protruding through an opening of the housing, and a shearing template fixedly arranged on a distal end of the stem, said shearing template having a concave distal surface and a side surface tapered in a proximal direction,
   a pair of arms, each having a distal end provided with a semi-annular blade, each arm being rotatable about an axis perpendicular to an extension axis of the stem, between an open position and a shearing position in which the semi-annular blades are closed to form a ring perpendicular to the extension axis of the stem and have a cutting edge which engages the side surface of the shearing template, and
   an actuating mechanism for controlling rotation of the arms in response to an actuation of the control member,
   wherein each semi-annular blade has a main working surface which has a curved profile and is tapered in the proximal direction and on which the cutting edge is arranged, said cutting edge forming a closed curve when the blades are in the shearing position,
   wherein each blade has a pair of secondary working surfaces arranged on diametrically opposite sides of the main working surface of the respective blade, the secondary working surfaces of one of the blades engaging the secondary working surfaces of the other blade when the blades are in the shearing position,
   wherein the pair of secondary working surfaces of one of the blades is provided with a secondary cutting edge, the other pair of secondary working surfaces being provided with a groove for receiving the respective secondary cutting edge when the blades are in the shearing position.

2. The circumcision device according to claim 1, wherein, in the shearing position, the cutting edge of the semi-annular blades engages the side surface of the shearing template at a point having an abrupt variation in inclination.

3. The circumcision device according to claim 1, wherein the actuating mechanism comprises an inner barrel and an outer barrel arranged coaxially with the stem, the inner barrel being translationally integral with the stem and the outer barrel being translatable along the stem, wherein each arm has a proximal end hinged together with the inner barrel and is rotationally actuatable by a translation of the outer barrel, and wherein the actuating mechanism is designed to control the translation of the outer barrel in response to an actuation of the control member.

4. The circumcision device according to claim 3, wherein a handling ring rotatable around the stem is arranged at the opening of the housing, said handling ring being rotationally integral with the inner barrel and the outer barrel.

5. The circumcision device according to claim 3, wherein said at least one control member comprises a hand-actuatable lever, and the actuating mechanism is configured to transform a rotation of the lever into at least one of: a rotation of the arms and a translation of the outer barrel.

6. The circumcision device according to claim 5, wherein the actuating mechanism is configured to automatically lock the blades in the shearing position at the end of a closing movement of the arms.

7. The circumcision device according to claim 6, wherein said at least one control member comprises a release member actuatable by hand for unlocking the blades from the shearing position, the actuating mechanism being configured to bias the arms into the open position.

8. A circumcision device, comprising:
a housing comprising a handgrip part integral with the housing, wherein at least one control member is arranged on the handgrip part,
a guide part comprising a stem integral with the housing, said stem being arranged partially within the housing and outwardly protruding through an opening of the housing, and a shearing template fixedly arranged on a distal end of the stem, said shearing template having a concave distal surface and a side surface tapered in a proximal direction,
a pair of arms, each having a distal end provided with a semi-annular blade, each arm being rotatable about an axis perpendicular to an extension axis of the stem, between an open position and a shearing position in which the semi-annular blades are closed to form a ring perpendicular to the extension axis of the stem and have a cutting edge which engages the side surface of the shearing template, and
an actuating mechanism for controlling rotation of the arms in response to an actuation of the control member,
wherein the actuating mechanism comprises an inner barrel and an outer barrel arranged coaxially with the stem, the inner barrel being translationally integral with the stem and the outer barrel being translatable along the stem,
wherein each arm has a proximal end hinged together with the inner barrel and is rotationally actuatable by a translation of the outer barrel, and
wherein the actuating mechanism is designed to control the translation of the outer barrel in response to an actuation of the control member,
wherein a handling ring rotatable around the stem is arranged at the opening of the housing, said handling ring being rotationally integral with the inner barrel and the outer barrel.

9. The circumcision device according to claim 8, wherein, in the shearing position, the cutting edge of the semi-annular blades engages the side surface of the shearing template at a point having an abrupt variation in inclination.

10. The circumcision device according to claim 8, wherein each semi-annular blade has a main working surface which has a curved profile and is tapered in the proximal direction and on which the cutting edge is arranged, said cutting edge forming a closed curve when the blades are in the shearing position.

11. The circumcision device according to claim 10, wherein each blade has a pair of secondary working surfaces arranged on diametrically opposite sides of the main working surface of the respective blade, the secondary working surfaces of one of the blades engaging the secondary working surfaces of the other blade when the blades are in the shearing position.

12. The circumcision device according to claim 8, wherein said at least one control member comprises a hand-actuatable lever, and the actuating mechanism is configured to transform a rotation of the lever into at least one of: a rotation of the arms and a translation of the stem.

13. The circumcision device according to claim 12, wherein the actuating mechanism is configured to automatically lock the blades in the shearing position at the end of a closing movement of the arms.

14. The circumcision device according to claim 13, wherein said at least one control member comprises a release member actuatable by hand for unlocking the blades from the shearing position, the actuating mechanism being configured to bias the arms into the open position.

* * * * *